United States Patent

Hybler

[11] Patent Number: 5,915,433
[45] Date of Patent: Jun. 29, 1999

[54] COMBINED TOOTHBRUSH AND TONGUE SCRAPER WITH ANTI-SLIP BUMPS THEREBETWEEN

[76] Inventor: Iva Hybler, 10 Weston Ave., Apt. 222, Quincy, Mass. 02170-1842

[21] Appl. No.: 08/967,638

[22] Filed: Nov. 10, 1997

[51] Int. Cl.⁶ .............................. A47L 13/12; A46B 9/04; A61B 17/24
[52] U.S. Cl. .......................... 15/111; 15/143.1; 15/167.1; 606/161
[58] Field of Search .................................. 15/111, 167.1, 15/143.1; 606/161, 162

[56] References Cited

U.S. PATENT DOCUMENTS

| D. 122,815 | 10/1940 | Crosby | 15/111 X |
|---|---|---|---|
| 2,574,654 | 11/1951 | Moore | 15/111 |
| 4,488,327 | 12/1984 | Snider | 15/111 |
| 5,027,463 | 7/1991 | Daub | 15/167.1 X |
| 5,623,739 | 4/1997 | Thompson | 15/143.1 X |

Primary Examiner—Elizabeth McKane

[57] ABSTRACT

A combined toothbrush and tongue scraper with anti-slip bumps therebetween including an elongated one-piece plastic base portion having a first end and a second end and with an intermediate extent therebetween, an integral tongue scraper formed at the first end having two symmetric legs with a cross-piece therebetween thereby creating an isosceles triangle with the apex angle being formed with the intermediate extent, the cross-piece having teeth, a plurality of bristles formed at the second end; and the intermediate extent being formed in a configuration with opposed faces and with a plurality of hemispherical bumps integrally formed in the opposed planar faces.

3 Claims, 3 Drawing Sheets

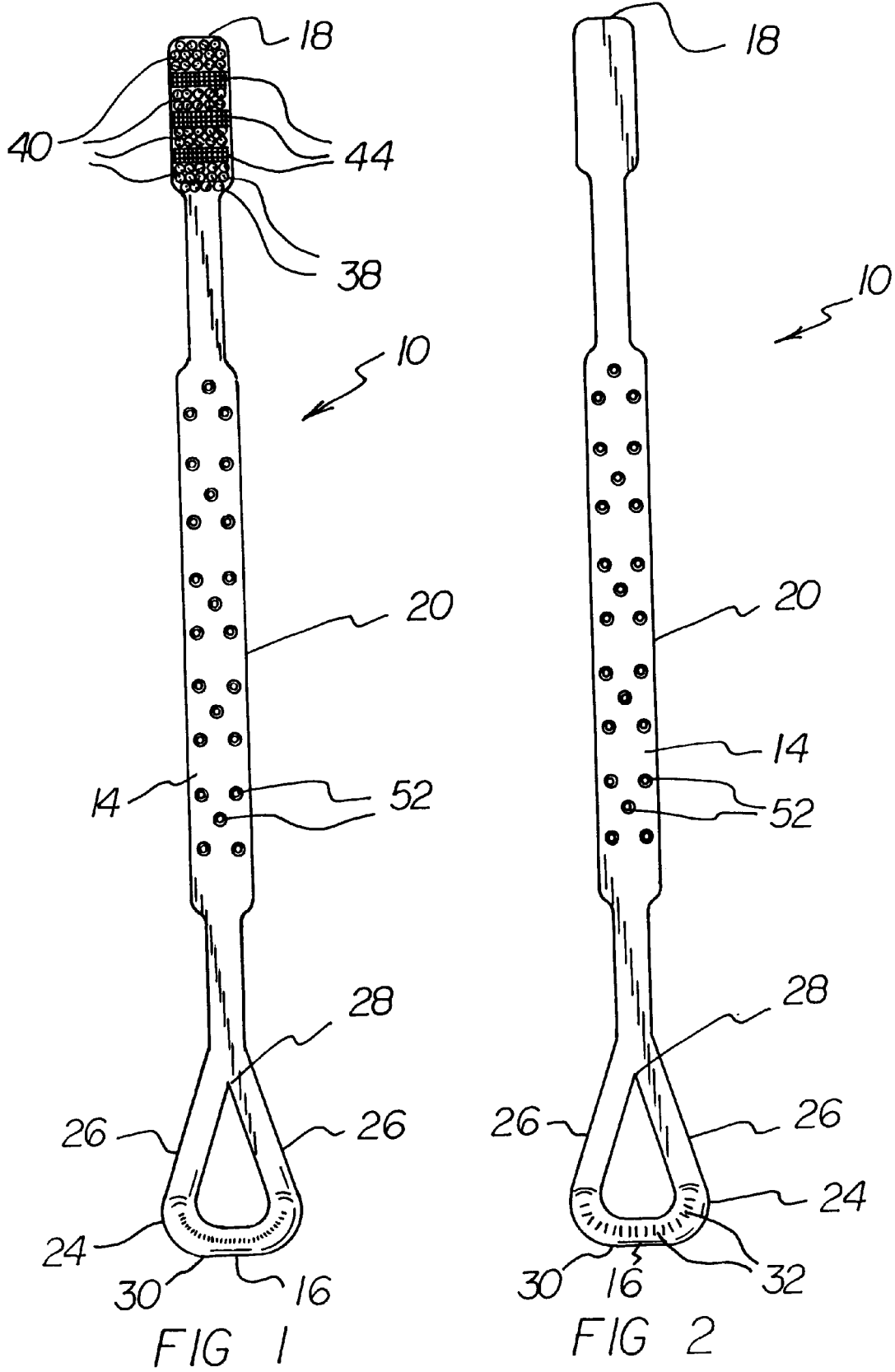

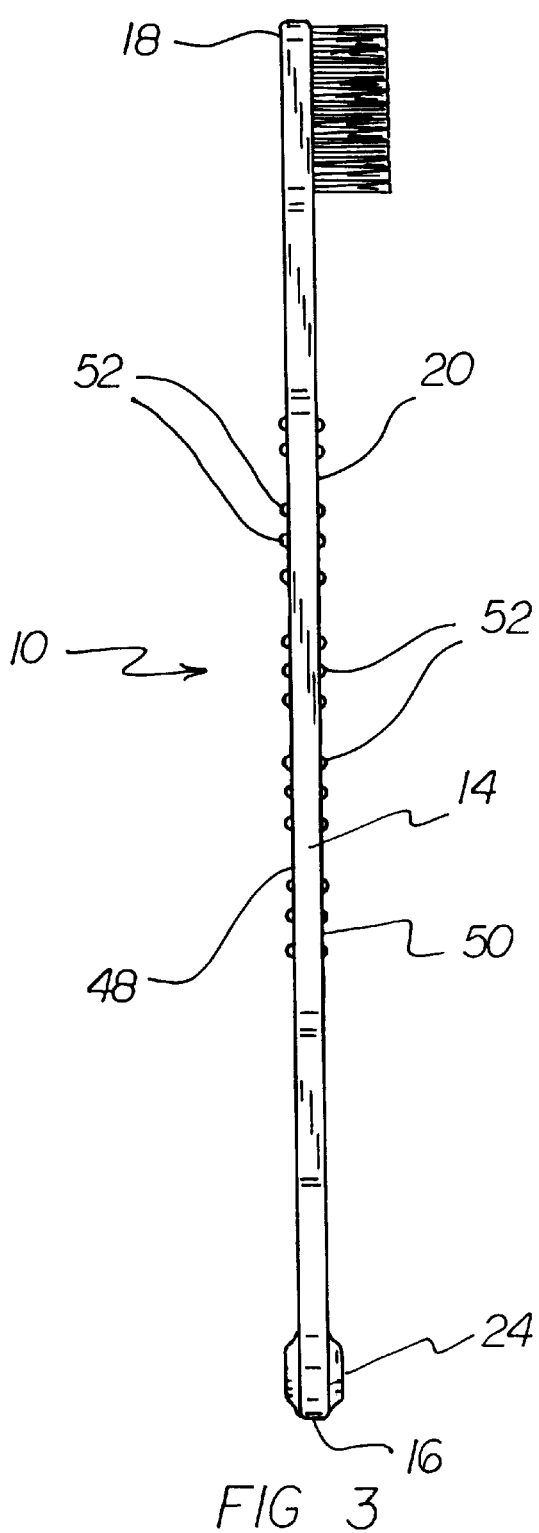
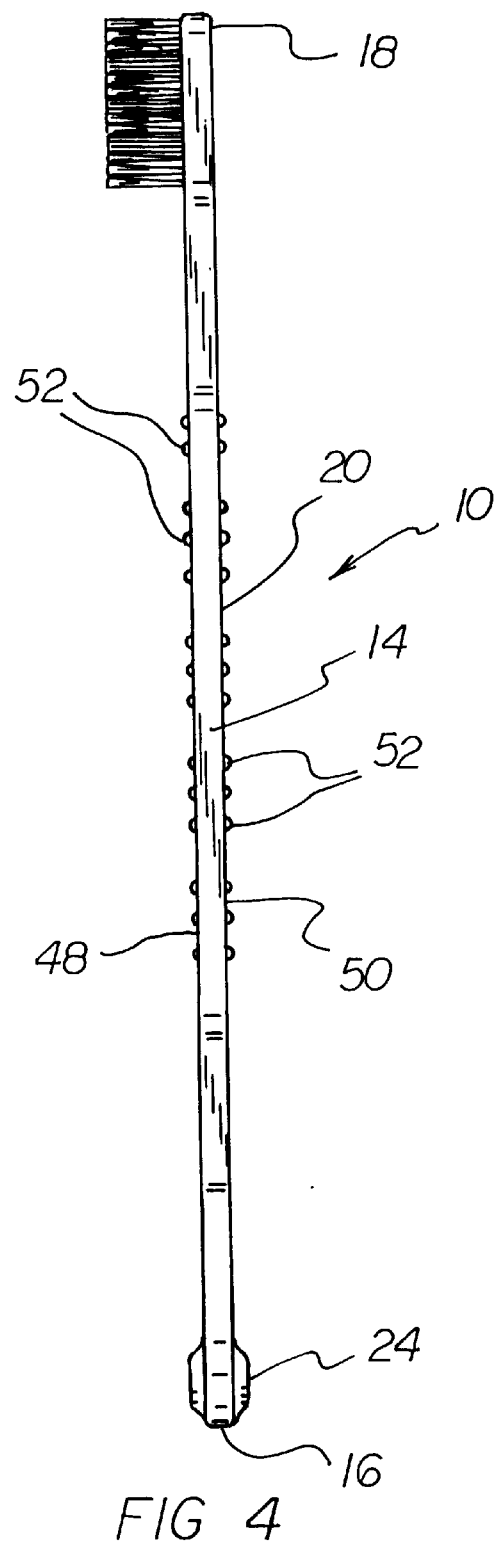

COMBINED TOOTHBRUSH AND TONGUE SCRAPER WITH ANTI-SLIP BUMPS THEREBETWEEN

BACKGROUND OF THE INVENTION

1. Field of the Invention

The present invention relates to a combined toothbrush and tongue scraper with anti-slip bumps therebetween and more particularly pertains to promoting oral hygiene through a combination tooth brush and tongue scraper.

2. Description of the Prior Art

The use of devices for promoting oral hygiene through various methods and apparatuses is known in the prior art. More specifically, promoting oral hygiene through various methods and apparatuses heretofore devised and utilized for the purpose of promoting oral hygiene through methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 2,574,654 to Moore discloses a multi-piece device for cleaning a tongue and for rushing teeth. Other patents show various tongue cleaners and various toothbrushes by themselves.

While these devices fulfill their respective, particular objectives and requirements, the aforementioned patents do not describe a one-piece combined toothbrush and tongue scraper with anti-slip bumps therebetween that allow simplified oral hygiene.

In this respect, the combined toothbrush and tongue scraper with anti-slip bumps therebetween according to the present invention substantially departs from the conventional concepts and designs of the prior art, and in doing so provides an apparatus primarily developed for the purpose of promoting oral hygiene through a combination tooth brush and tongue scraper.

Therefore, it can be appreciated that there exists a continuing need for a new and improved combined toothbrush and tongue scraper with anti-slip bumps therebetween which can be used for Promoting oral hygiene through a combination tooth brush and tongue scraper. In this regard, the present invention substantially fulfills this need.

SUMMARY OF THE INVENTION

In view of the foregoing disadvantages inherent in the known types of Toothbrushes and tongue scrapers of various designs and configurations now present in the prior art, the present invention provides an improved combined toothbrush and tongue scraper with anti-slip bumps therebetween. As such, the general purpose of the present invention, which will be described subsequently in greater detail, is to provide a new and improved combined toothbrush and tongue scraper with anti-slip bumps therebetween and method which has all the advantages of the prior art and none of the disadvantages.

To attain this, the present invention essentially comprises a new and improved combined toothbrush and tongue scraper with anti-slip bumps therebetween comprising, in combination an elongated one-piece plastic base portion having a first tongue scraping end and a second tooth brushing end and with an intermediate handle extent therebetween, an integral tongue scraper formed at the first end having two symmetric legs forming an apex angle with a cross-piece therebetween thereby creating an isosceles triangle with the apex angle being integrally formed with the intermediate handle extent, the cross-piece having teeth, the teeth having spaced interior arcuate recesses with linear exterior faces therebetween and formed therein for movement along the tongue to remove unwanted materials from a user's tongue, a plurality of bristles formed at the second end, the bristles including a plurality of sections of conventional bristles formed as staggered columns and rows of flexible tufts with a plurality of rows of hard semi-rigid sweeping material between the sections of tufts for brushing a user's teeth; and the intermediate extent being formed in a generally flat configuration with opposed planar faces and with a plurality of hemispherical bumps integrally formed in the opposed planar faces in staggered rows and columns to preclude slipping in a user's hand when either brushing teeth with the second end or scraping a tongue with the first end.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved combined toothbrush and tongue scraper with anti-slip bumps therebetween which has all of the advantages of the prior art Toothbrushes and tongue scrapers of various designs and configurations and none of the disadvantages.

It is another object of the present invention to provide a new and improved combined toothbrush and tongue scraper with anti-slip bumps therebetween which may be easily and efficiently manufactured and marketed.

It is further object of the present invention to provide a new and improved combined toothbrush and tongue scraper with anti-slip bumps therebetween which is of durable and reliable constructions.

An even further object of the present invention is to provide a new and improved combined toothbrush and tongue scraper with anti-slip bumps therebetween which is susceptible of a low cost of manufacture with regard to both materials and labor, and which accordingly is then susceptible of low prices of sale to the consuming public, thereby making such combined toothbrush and tongue scraper with anti-slip bumps therebetween economically available to the buying public.

Even still another object of the present invention is to provide a combined toothbrush and tongue scraper with anti-slip bumps therebetween for promoting oral hygiene through a combination tooth brush and tongue scraper.

Lastly, it is an object of the present invention to provide a combined toothbrush and tongue scraper with anti-slip bumps therebetween including an elongated one-piece plastic base portion having a first end and a second end and with an intermediate extent therebetween, an integral tongue scraper formed at the first end having two symmetric legs with a cross-piece therebetween thereby creating an isosceles triangle with the apex angle being formed with the intermediate extent, the cross-piece having teeth, a plurality of bristles formed at the second end; and the intermediate extent being formed in a configuration with opposed faces and with a plurality of hemispherical bumps integrally formed in the opposed planar faces.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention. dr

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of the preferred embodiment of the combined toothbrush and tongue scraper with anti-slip bumps therebetween constructed in accordance with the principles of the present invention.

FIG. 2 is a rear elevational view thereof.

FIG. 3 is a right side elevational view thereof.

FIG. 4 is a left side view thereof.

The same reference numerals refer to the same parts through the various Figures.

DESCRIPTION OF THE PREFERRED EMBODIMENT

Figure 5:
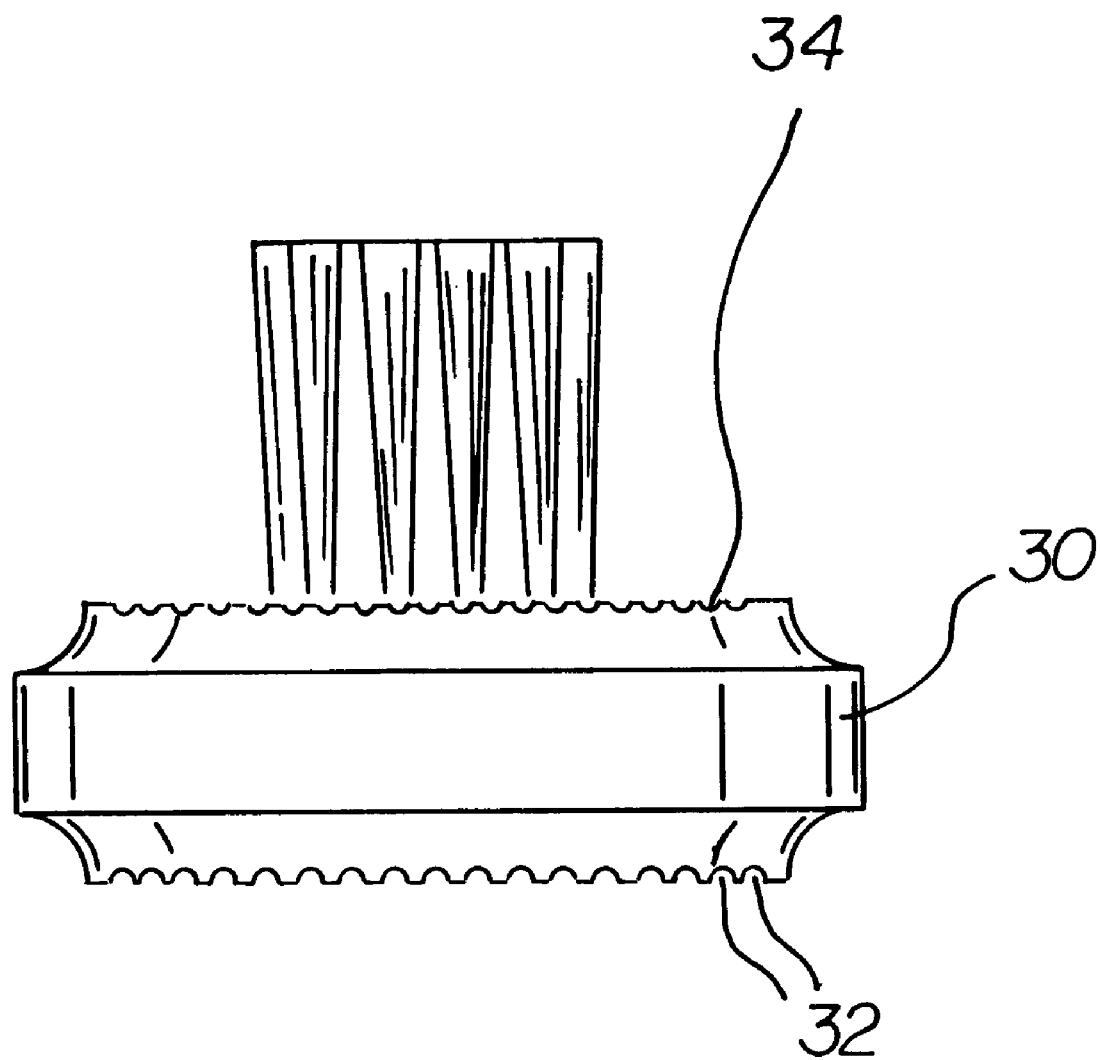
FIG. 5 is a perspective view of the scraping end of the device shown in FIGS. 1–4.

With reference now to the drawings, and in particular to FIG. 1 thereof, the preferred embodiment of the new and improved combined toothbrush and tongue scraper with anti-slip bumps therebetween embodying the principles and concepts of the present invention and generally designated by the reference numeral 10 will be described.

The present invention, a combined toothbrush and tongue scraper 10 with anti-slip bumps therebetween 10 is comprised of a plurality of components. Such components in their broadest context include a base portion, a tongue scraper, bristles and an intermediate extent. Such components are individually configured and correlated with respect to each other so as to attain the desired objective.

Specifically, the present invention includes an elongated one-piece plastic base portion 14. The base portion has a first tongue scraping end 16 and a second toothbrushing end 18. An intermediate handle extent 20 is located between the first tongue scraping end and the second toothbrushing end.

Formed at the first end is an integral tongue scraper 24. The scraper is formed to have two symmetric legs 26. The legs form an apex angle 28. In addition, a cross-piece 30 extends between the ends of the symmetric legs remote from the intermediate handle extent. The legs and cross-piece together form an isosceles triangle. The apex angle 28 of the triangle is formed integrally with the intermediate handle extent.

In the preferred embodiment, the cross-piece is formed having undulating teeth on opposite sides of the cross-piece.

The undulating teeth are formed integrally into the plastic material. The teeth include spaced interior arcuate recesses and spaced exterior arcuate recesses which together form coarse undulations 34 to give a relatively rough scraping of the tongue when dragged thereacross for the removal of unwanted materials including germs and plaque. The teeth on the opposite side of the cross-piece also include spaced interior arcuate recesses and spaced exterior arcuate recesses which together form fine undulations 36. The radius of the undulations 36 are smaller than the radii of the undulations 34 to give a relatively gentle scraping of the tongue.

The next component of the system are a plurality of bristles 38. The bristles are formed at the second end. The bristles include a plurality of sections 40 of conventional bristles. They are preferably formed of synthetic fibers of materials conventional in the toothbrushing art. The bristles are formed in staggered rows and columns with the bristles of conventional length, diameter and spacing and form flexible tufts. In addition, a plurality of rows of harder, semi-rigid sweeping bristles 44 are located between the sections of tufts. Such sweeping bristles are preferably formed of finer, firmer, more closely spaced bristles than is conventional. Such sweeping bristles in combination with the conventional tufts are for a combined brushing and sweeping of a user's teeth in a manner superior than conventional toothbrushes due to the action of the brushing and sweeping.

Lastly provided as a component of the system is the intermediate extent 20. The intermediate extent is formed in a generally flat configuration with opposed planar faces 48 and 50. In addition, both planar faces are formed with a plurality of hemispherical bumps 52. Such bumps are integrally formed on the opposed planar faces in staggered rows and columns. The purpose of the bumps is to preclude slipping of the device in a user's hand when the user is either brushing his or her teeth with the second end or scraping his or her tongue with the first end.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the united states is as follows:

1. A new and improved combined toothbrush and tongue scraper with anti-slip bumps therebetween comprising, in combination:

an elongated one-piece plastic base portion having a first tongue scraping end and a second tooth brushing end and with an intermediate handle extent therebetween;

an integral tongue scraper formed at the first end having two symmetric legs forming an apex angle with a cross-piece therebetween thereby creating an isosceles triangle with the apex angle being integrally formed with the intermediate handle extent, the cross-piece having teeth formed of undulations of one side having a greater radii than the undulations of the other side for movement along the tongue to remove unwanted materials from a user's tongue;

a plurality of bristles formed at the second end, the bristles including a plurality of sections of conventional bristles formed as staggered columns and rows of flexible tufts with a plurality of rows of hard semi-rigid sweeping bristles between the sections of tufts for brushing a user's teeth; and the intermediate extent being formed in a generally flat configuration with opposed planar faces and with a plurality of hemispherical bumps integrally formed in the opposed planar faces in staggered rows and columns to preclude slipping in a user's hand when either brushing teeth with the second end or scraping a tongue with the first end.

2. A combined toothbrush and tongue scraper comprising:

an elongated one-piece plastic base portion having a first end and a second end and with an intermediate extent therebetween;

an integral tongue scraper formed at the first end having two symmetric legs with a cross-piece therebetween thereby creating an isosceles triangle with the apex angle being formed with the intermediate extent, the cross-piece having teeth;

a plurality of bristles formed at the second end; and the intermediate extent being formed in a configuration with opposed faces and with a plurality of hemispherical bumps integrally formed in the opposed planar faces;

wherein the cross-piece has teeth formed of undulations of one side having a greater radii than the undulations of the other side for movement along the tongue to remove unwanted materials from a user is tongue.

3. The apparatus as set forth in claim 2 wherein the bristles include a plurality of sections of conventional bristles formed as staggered columns and rows of flexible tufts with a plurality of rows of hard semi-rigid sweeping bristles between the sections of tufts for brushing a user's teeth.

* * * * *